(12) United States Patent
Vilser

(10) Patent No.: US 8,098,908 B2
(45) Date of Patent: Jan. 17, 2012

(54) METHOD AND DEVICE FOR ANALYZING THE RETINAL VESSELS BY MEANS OF DIGITAL IMAGES

(75) Inventor: Walthard Vilser, Rudolstadt (DE)

(73) Assignee: IMEDOS GmbH, Jena (DE)

( * ) Notice: Subject to any disclaimer, the term of this patent is extended or adjusted under 35 U.S.C. 154(b) by 1277 days.

(21) Appl. No.: 11/663,380

(22) PCT Filed: Sep. 21, 2005

(86) PCT No.: PCT/DE2005/001680
§ 371 (c)(1),
(2), (4) Date: Mar. 21, 2007

(87) PCT Pub. No.: WO2006/032261
PCT Pub. Date: Mar. 30, 2006

(65) Prior Publication Data
US 2008/0107310 A1    May 8, 2008

(30) Foreign Application Priority Data

Sep. 21, 2004 (DE) .................. 10 2004 046 141

(51) Int. Cl.
*G06K 9/00* (2006.01)
(52) U.S. Cl. .................... 382/128; 382/100; 382/151
(58) Field of Classification Search .................. 382/100, 382/128
See application file for complete search history.

(56) References Cited

U.S. PATENT DOCUMENTS 5,674,405 A * 10/1997 Bourhis et al. ................ 210/761

(Continued)

FOREIGN PATENT DOCUMENTS

WO    02/15818    2/2002

OTHER PUBLICATIONS

XP008057215 Biosciences Information Service, Philadelphia, PA, US Jun. 2004, vol. 111, No. 6, pp. 1183-1190 "Computer-Assisted Measurement of Retinal Vessel Diameters in the Beaver Dam Eye Study" Tien Yin Wong, et al.

(Continued)

*Primary Examiner* — Jingge Wu
*Assistant Examiner* — Avinash J Yentrapati
(74) *Attorney, Agent, or Firm* — Frommer Lawrence & Haug LLP

(57) ABSTRACT

It is the object of a method and apparatus for retinal vessel analysis based on digital images to enhance the ability to discriminate between healthy vessel states and at-risk vessel states while reducing manual effort and saving time in order to allow individual vascular risk, particularly stroke risk, to be determined in a more reliable manner and with fewer subjective systematic and random errors. The vessel segment diameter, type of vessel and the image coordinates are determined for a series of adjoining vessel segments along vessel portions in a measurement zone surrounding the papilla and are stored by vessel segment with reference to the evaluated image, to a reference image recorded with a time offset, and to a displacement vector that is determined for the vessel segment between the reference image and an evaluated comparison image. Comparison measurements are carried out only on identical vessel segments already measured in the reference image. The correlation of vessel segments to vessel portions and to vessel type is adopted intact from the reference image. The stored data sets for the vessel segments of the reference image and comparison images provide a progression of coordinate-oriented vessel segment diameters for all measured vessel segments as basis for determining parameters and presenting them in a spatially resolved progression, e.g., in progress images.

15 Claims, 1 Drawing Sheet

U.S. PATENT DOCUMENTS

| | | | |
|---|---|---|---|
| 5,754,681 A * | 5/1998 | Watanabe et al. | 382/159 |
| 5,912,720 A * | 6/1999 | Berger et al. | 351/206 |
| 5,935,076 A * | 8/1999 | Smith et al. | 600/479 |
| 5,993,001 A | 11/1999 | Bursell et al. | |
| 6,621,917 B1 * | 9/2003 | Vilser | 382/128 |
| 6,623,431 B1 * | 9/2003 | Sakuma et al. | 600/443 |
| 6,741,880 B1 * | 5/2004 | Foo et al. | 600/419 |
| 6,913,888 B2 * | 7/2005 | Schwartz et al. | 435/6 |
| 7,054,476 B2 * | 5/2006 | Oosawa et al. | 382/132 |
| 7,742,629 B2 * | 6/2010 | Zarkh et al. | 382/128 |
| 7,796,796 B2 * | 9/2010 | Camus et al. | 382/130 |
| 2003/0055608 A1 | 3/2003 | Beerends et al. | |
| 2003/0216650 A1 | 11/2003 | Michelson | |
| 2006/0036167 A1 * | 2/2006 | Shina | 600/433 |
| 2006/0058643 A1 * | 3/2006 | Florent et al. | 600/423 |
| 2008/0247621 A1 * | 10/2008 | Zarkh et al. | 382/130 |

OTHER PUBLICATIONS

XP002061911 Current Eye Research, IRL Press, Oxford, GB, vol. 15, No. 6, Jun. 1, 1996, pp. 625-632 "The accurate assessment of changes in retinal vessel diameter using multiple frame electrocardiograph synchronised fundus photography" Martin J. Dumskyj, et al.

XP008057309 Biosciences Information Service, Philadelphia, PA, US, Dec. 1999, vol. 106, No. 12, pp. 2269-2280 "Methods for Evaluation of Retinal Microvascular Abnormalities Associated with Hypertension/Sclerosis in the Atherosclerosis Risk in Communities Study" Larry D. Hubbard, et al.

XP008057311 American Journal of Ophthalmology, Apr. 1974, vol. 77, No. 4, pp. 478-483 "Mathematic Relationships Between the Width of a Retinal Artery and the Widths of its Branches" J.C. Parr, et al.

XP008057224 Clinical and Experimental Ophthalmology, Jun. 2002, vol. 30, No. 3, pp. 179-182 "Reliability of Computer-Assisted Retinal Vessel Measurement in a Popilation" Lauren M. Sherry, et al.

XP002360139 Excerpt from Basic Fluid Dynamics Principles—Application to Percutaneous Intervention (online / www.emedicine.com) Oct. 20, 2003, pp. 1-2.

* cited by examiner

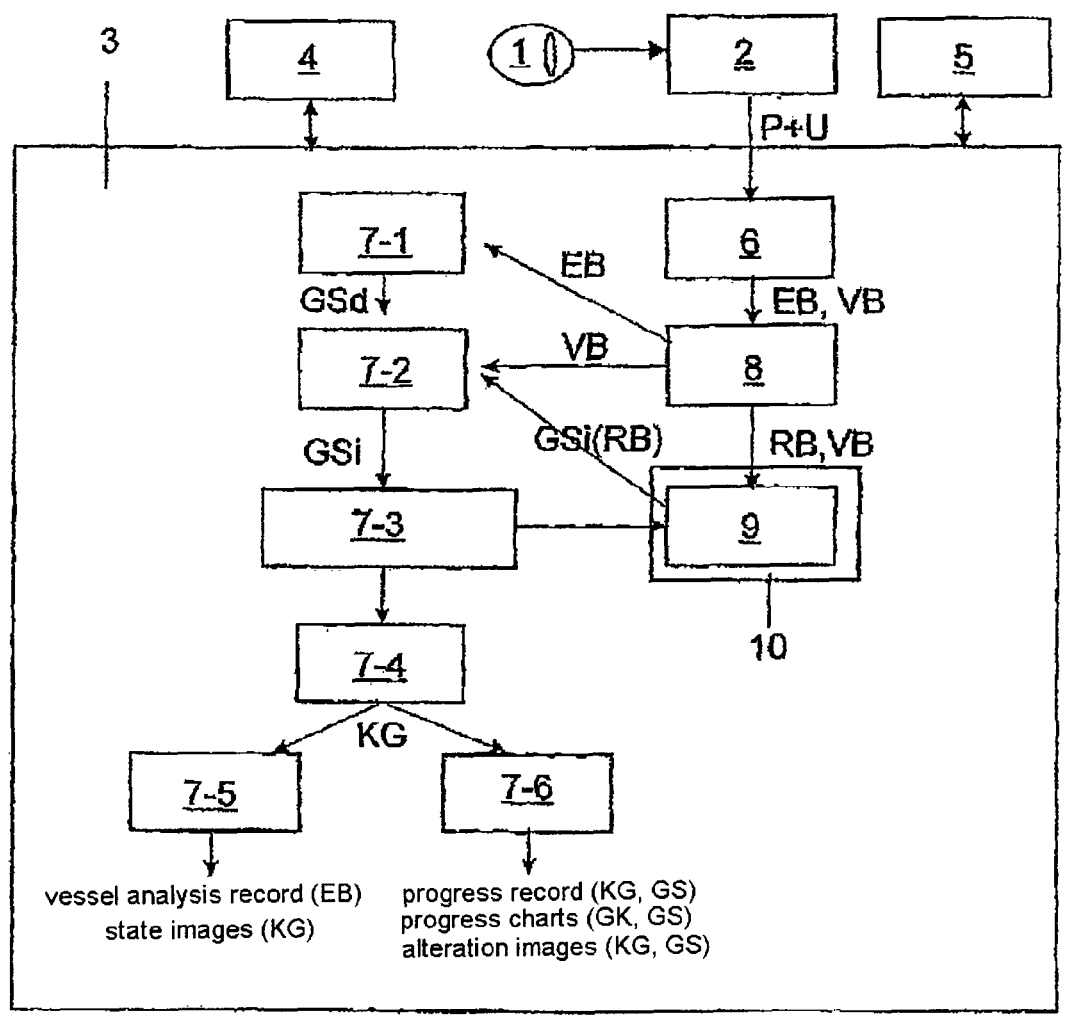

METHOD AND DEVICE FOR ANALYZING THE RETINAL VESSELS BY MEANS OF DIGITAL IMAGES

CROSS-REFERENCE TO RELATED APPLICATIONS

This application claims priority of International Application No. PCT/DE2005/001680, filed Sep. 21, 2005 and German Application No. 10 2004 046 141.4, filed Sep. 21, 2004, the complete disclosures of which are hereby incorporated by reference.

BACKGROUND OF THE INVENTION a) Field of the Invention

The invention is directed to a method for the analysis of retinal vessels based on digital images in which a ring-shaped measurement zone containing vessel portions which proceed from a central vessel and are to be measured and which differ in type between arteries and veins is arranged around the papilla, a vessel diameter being determined for each of these vessel portions, and parameters are calculated from the determined vessel diameters of the vessel portions.

The invention is further directed to an apparatus for the analysis of retinal vessels based on digital images containing a mydriatic or nonmydriatic retinal camera for recording images, a controlling and evaluating computer provided with data input media and data output media and having a system that acquires, stores and archives correlated image data and patient data, means for determining a ring-shaped measurement zone surrounding the papilla in the images which contains vessel portions which proceed from a central vessel and which are to be measured, a measuring device for determining the vessel diameter, and calculating means for determining parameters from the measured vessel diameters.

b) Description of the Related Art

By means of a quantitative vessel analysis using digital images of the fundus, it is possible to assess vascular risk which can be determined, e.g., by means of an arteriole-to-venule ratio according to Hubbard et al. (Ophthalmology, Vol. 106, December 1999, pages 2269-2280) as A/V(PSH) ratio. For example, in a study (ARIC study) it was possible to determine a relationship between the A/V ratio and the cardiovascular risk in women and for stroke and diabetes in women and men independent from blood pressure and other risk factors.

The digital fundus images are evaluated in that the A/V (PSH) ratio is calculated as a parameter by a predetermined formula from vessel diameters of arteries and veins measuring above a limiting value which are located within a ring-shaped measurement zone around the papilla. For this purpose, a central arteriolar equivalent CAE(PSH) and a central venular equivalent CVE(PSH) are calculated from the vessel diameters of all of the measured arteries and all of the measured veins based on Hubbard's formula (Ophthalmology, Vol. 106, December 1999, page 2272). The A/V(PSH) ratio is determined as a quotient: CAE(PSH)/CVE(PSH).

Wong et al. (Ophthalmology, Vol. 111, June 2004, 1183-1190) suggest selecting a small piece of a large vessel portion from the vessels identified as arteries and veins within the measurement zone and determining a mean vessel diameter characterizing the entire vessel from five measurements per vessel piece to include in the calculation of the A/V(PSH) ratio.

Because of the high measurement uncertainty with a method-related standard deviation over a number of classification limits in determining the parameters and because of the high inter-individual variability, individual follow-ups and the comparison of an individual A/V(PSH) ratio to a healthy test group have only a limited ability to discriminate between healthy individuals and those with an increased stroke risk and consequently are less suitable for individual diagnoses. In addition, the assessment of follow-ups and comparison to healthy measurements in the known method described by Wong et al. is time-consuming. Further, there is a high incidence of subjective systematic and random errors due to the manual and semi-manual implementation of the method.

OBJECT AND SUMMARY OF THE INVENTION

Therefore, it is the primary object of the invention to enhance the ability to discriminate between healthy vessel states and at-risk vessel states while reducing manual effort and saving time in order to allow individual vascular risk, particularly stroke risk, to be determined in a more reliable manner and with fewer subjective systematic and random errors.

This object is met in a method for retinal vessel analysis of the type mentioned above in accordance with the invention, based on digital images comprising the steps of: arranging a ring-shaped measurement zone containing vessel portions which proceed from a central vessel and are to be measured and which differ in type between arteries and veins, the zone being arranged around the papilla at a distance therefrom; determining a vessel diameter for each of these vessel portions; selecting a series of adjoining vessel segments along the vessel portions; determining a vessel segment diameter and the associated image coordinates for every segment; correlating the vessel segment to a vessel type distinguished by artery or vein and to a vessel portion; and storing and archiving a data set comprising at least the coordinates of the vessel segment, the vessel diameter, the associated vessel type, the associated vessel portion and a relatedness to the evaluated image for every vessel segment.

DETAILED DESCRIPTION OF THE INVENTION AND PREFERRED EMBODIMENTS

A series of adjoining vessel segments is selected along the vessel portions, and a vessel segment diameter, assignment to a vessel portion, the type of vessel distinguished by artery or vein and the associated image coordinates are determined for every vessel segment and are stored and archived by vessel segment together in a data set with reference to the evaluated image so that they can be accessed for subsequent comparison measurements. By means of comparison measurements in comparison images of the same eye recorded at offset times, the vessel diameters are automatically determined in the comparison image for vessel segments identical to a selected reference image, wherein the correlation of the vessel segment to the vessel type and vessel portion is adopted intact from the reference image. The data sets relating to the vessel segment in the comparison images are supplemented by reference to the reference image and a displacement vector of the vessel segment between the reference image and the comparison image. The vessel segment-related data sets in the reference image and the vessel segment-related data sets in the comparison images referencing the reference image provide time progressions in a database for exactly comparable vessel segment diameters. According to the invention, meaningful parameters are formed on this basis and are clearly represented in graphs or flowcharts which appreciably enhance the ability to discriminate between healthy and diseased vessels and the meaningfulness of the microvascular risk.

In contrast to Wong et al., the procedure according to the invention, in which measurements are preferably taken for all of the vessel segments detectable within a measurement zone, can provide advantageous information derived from the diameter curve of vessel portions by generating parameters for these vessel portions according to a definable protocol. Functional and pathological vascular changes such as narrowing and dilatation can be detected because, rather than considering only one individual value as representative for a vessel, location-dependent measurements are now carried out at the vessels, which substantially increases the validity of the examination method. Application of the method is also advantageous because measurement uncertainty is inversely proportional to the length of the vessel.

The invention advantageously offers the possibility of comparison measurements when at least one examination has already been carried out on the eye of the same patient and the measurement values and image from this examination can be accessed by the apparatus used for carrying out the method, i.e., they are stored in memory.

Accordingly, when carrying out patient-oriented comparison measurements in comparison images that have been recorded with a time offset to the reference image, the diameters of vessel segments in the comparison image which are identical to the vessel segments in the reference image are determined, and the correlation of the vessel type and vessel portion to every vessel segment is adopted intact in the data set of the comparison image from the data set of the reference image, and the data sets relating to the vessel segments of the comparison image are expanded at least by the relatedness to the reference image.

In an advantageous manner, the coordinates for vessel segments in the comparison image are calculated from the coordinates of the vessel segments in the reference image by means of previously determined displacement vectors so that the measurement of the diameters of vessel segments in the comparison image that are identical to the vessel segments in the reference image can be carried out automatically. In so doing, the data sets of the vessel segments of the comparison image are expanded at least by the displacement vector of the vessel segment.

Due to the fact that the image coordinates of all of the measurement locations in the comparison images that were determined only once in the reference image are spatially corrected and, like the correlations to the vessel type that were determined once in the reference image and retained, are given automatically for the measurements in the comparison images, measurements in the comparison images are always carried out at the locations where the image contents are identical to those in the selected reference image so that only measured values of exactly identical locations and identical correlations (quadrants, artery correlation, vein correlation) are included in the determination and display of individual changes in course regardless of the image sequence to be evaluated.

Also, it is especially significant that only identical vessel segments for which a vessel segment diameter can be determined in all of the comparison images and in the reference image are used for determining the parameters in comparison measurements of a plurality of comparison images, and that absolute and relative differences between the reference image and the comparison image are generated for the vessel diameters and parameters.

Accordingly, the net outcome is that an objective spatial correction and automatic preset of measurement locations and an objective selection of evaluable data sets which are unconditionally complete with respect to time and location in relation to any defined reference image of an image sequence, a given parameter or parameter vector is made possible regardless of whether or not the images or the measurement location coordinates are spatially corrected.

By generating differences between the vessel segment diameters from the reference image and those from the comparison image, or also from the differences between the parameters calculated from the vessel segment diameters, very sensitive changes in the microvascular state can be determined.

Parameters can be determined in a particularly advantageous manner in that a mean diameter used for determining parameters is formed as an arithmetic average for every vessel portion from the progression of vessel segment diameters.

As first and second parameters, a central arteriolar equivalent and a central venular equivalent can be determined from the mean diameters of the arteriolar vessel portions and the venular vessel portions and, as a third parameter, an arteriole-to-venule ratio can be derived therefrom which, while calculated based on Hubbard, delivers parameters based on the invention that are far more reproducible and more precise than in the prior art.

However, the central arteriolar equivalent and the central venular equivalent are preferably formed as $n^{th}$ roots from the sum of all $n^{th}$ powers of the mean vessel portion diameters, wherein a value for n between 2.5 and 3.0, preferably 2.7, is used for the central arteriolar equivalent, and a value for n between 2.0 and 2.5, preferably 2.1, is used for the central venular equivalent.

Also, for every vessel portion, a maximum diameter and a minimum diameter and the scatter of the mean vessel segment diameters can be determined as a fourth parameter vector.

Further, the reciprocal of the fourth power of the mean vessel segment radius can be formed as a fifth parameter for describing the vascular resistance of a vessel segment, and the quotient of the vessel length and vessel radius can be formed as a sixth parameter for describing the local pressure drop.

For the vessel segments, the vessel length is the vessel segment length which can be preset, but which must be updated by calculation in case of variable vessel segment length. The vessel radius is half of the vessel segment diameter in this case. In case of an entire vessel portion, the vessel length of the vessel portion must be calculated and the vessel radius is half of the mean vessel diameter of the vessel portion.

A further parameter can be determined by forming an inside value and an outside value, respectively, for a central arteriolar equivalent, a central venular equivalent and an arteriole-to-venule ratio from the mean vessel diameters of the vessel portions which lie closest to the inside boundary of the ring-shaped measurement zone and from the mean vessel diameters of the vessel portions lying closest to the outside boundary of the ring-shaped measurement zone.

As additional parameters for the vessel portions, a seventh, eighth and ninth parameter can be formed
  as root from the sum of all squares of the mean diameters of a vessel portion,
  as third root from the sum of all third powers of the mean diameters of a vessel portion, and
  as fourth root from the sum of all fourth powers of the mean diameters of a vessel portion, wherein
  the central equivalents for arteries and veins are determined from the seventh, eighth and ninth parameters, and the arteriole-to-venule ratio is formed from these central equivalents.

From these additional parameters, parameters can be derived for every vessel portion which can be used in an advantageous manner as threshold values for the detection of focal narrowing for four classifications in that the 1st, 2nd, 3rd or 4th power of a mean vessel portion diameter is less than the associated threshold N1 or N2, N3 or N4.

The absolute value of the parameters for detecting focal narrowing is arrived at as follows, where threshold values are given as percentages:

first parameter focal narrowing $N1$=percentage threshold value for $N1 \times$mean diameter of the vessel portion/100%, second parameter focal narrowing $N2$=percentage threshold value for $N2 \times$seventh parameter/100%, third parameter focal narrowing $N3$=percentage threshold value for $N3 \times$eighth parameter/100%, and fourth parameter focal narrowing $N4$=percentage threshold value for $N4 \times$ninth parameter/100%.

The method according to the invention makes it possible as before to manually mark the vessel segments interactively and to correlate them manually to vessel portions and vessel type so that they can then be measured by automatic or semi-automatic measurement modules. This is very time-consuming and prone to error. According to the invention, however, a comparison measurement can be carried out already in a fully automatic manner. The use of vessel trackers is also possible. In this case, it is no longer necessary to manually mark and correlate all of the vessel segments but rather only the starting segment for the vessel tracker, which then detects the other vessel segments of the vessel portion, tracks them, and sends the vessel segments to the measurement module for measuring. This measurement module then determines the vessel segment diameters. However, vessel segmenting and other methods also make it possible to automatically detect the vessel segments and correlate them to vessel portions and vessel type.

Accordingly, with the method according to the invention, parameters can be determined far more efficiently because the measuring time and evaluating time in all of the described embodiment forms is drastically reduced. Since the parameters have a high objectivity due to the reduction in subjective influences, a parameter comparison in comparison images is considerably more reproducible and precise than in known technical solutions, even without a reference measurement.

This is particularly advantageous for risk assessment which now need no longer (but still can) be carried out by comparing barely distinguishable populations of different, highly scattered risk groups, but which rather can be reduced to individually verifiable changes in course.

In another embodiment of the invention, differences between spatially resolved parameters of the comparison image and of the reference image are calculated and different images are generated from the reference image, in which different images the diameter differences or spatially resolved parameters or spatially resolved parameter differences determined, respectively, from the comparison measurements are entered in correct coordinates and with color coding.

Progress graphics can be produced in which the vessel diameters and/or the parameters or differences thereof between comparison images and the reference image are graphically represented as a function of the time of the image recording.

It is also advantageous when the determined parameters and parameter differences are documented in a summarized manner for data output in that the positions of the vessel segments are marked in the evaluated image in such a way that the vessel segment diameter is reproduced in a coded manner or the vessel portion is characterized. When coding is carried out in different colors, narrow and wide vessel regions can be shown clearly and in an advantageous manner for evaluation.

The above-stated object is further met according to the invention by an apparatus of the type mentioned in the beginning for retinal vessel analysis in that a vessel segmenting device detects the vessel segments and their vessel type distinguished by artery and vein, acquires coordinates of the vessel segments in the image and selects a series of adjoining vessel segments along the detected vessel portions and image coordinates, and a vessel segment storage is provided in which data sets for the vessel segments with the vessel segment diameter, which was determined by the measuring device for determining the vessel diameter of each vessel segment, are stored and archived together with the associated image coordinates, the associated vessel portion, the associated vessel type and a relatedness to the evaluated image.

The means according to the invention can be integrated in a device or spatially separate from one another so that, e.g., image recording, evaluation and display can be carried out in different locations. Remote data transmission of the images or evaluation results can also be carried out, e.g., via the Internet or other media.

The measuring device for determining vessel diameter and the means for detecting and distinguishing the vessel portions by arteries and veins are devices which preferably operate automatically so that the determination of the vessel segment diameters and the correlation to vessel type can be carried out automatically.

The apparatus according to the invention can be further developed in a particularly advantageous manner in that it further contains for the purpose of patient-oriented comparison measurements in comparison images that are recorded with a time offset to a reference image: a device for retrieving identical vessel segments which contains coordinate conversion means that calculate the image coordinates for identical vessel segments in the comparison image from the image coordinates of the vessel segments in the reference image; and a difference generator which determines measurement-specific and parameter-specific differences between a reference image and at least one comparison image and which generates differences between the measured vessel segment diameter and the parameters, color-codes spatially-resolved differences, and assembles them in different progress images with correct coordinates in the reference image.

An image selecting device can be used for selecting reference images and comparison images.

Further, a vessel analysis documenting unit can advantageously be provided for generating vessel analysis logs and clinical state images in which the diameters of the vessel segments or the spatially-resolved parameters are clearly presented for assessment, e.g., color-coded in the fundus image.

BRIEF DESCRIPTION OF THE DRAWING

The invention will be described more fully in the following with reference to the schematic drawing. The drawing shows an apparatus for retinal vessel analysis in a block diagram.

DESCRIPTION OF THE PREFERRED EMBODIMENT SHOWN IN THE DRAWING

The manner in which the apparatus is shown in the drawing was chosen to facilitate understanding; however, structural optimizing could be achieved by corresponding reference to the state of the art.

A nonmydriatic or mydriatic retinal camera 2 with digital imaging or a digitizing system for fundus photography is provided for examining the eye 1 of a patient and communicates with a computer 3. Input media 4, e.g., a keyboard and mouse, serving for dialog mode and output media 5, e.g., a screen and printer, for the dialog and for displaying and outputting results are connected to the retinal camera 2.

A preferred imaging system 6 serves to acquire, store and archive image data and patient data, wherein a referenced connection can be made by means of an image identification (image ID) for each individual image EB between the patient data and examination data P and U stored in the imaging system 6, e.g., patient ID, right/left eye, date and time of examination, and the other data to be determined in particular according to the invention, e.g., vessel segment data sets GSi.

Instead of the imaging system 6, other means can also be provided which store at least data for definite identification of patients, of the examined eye, and of the date and time of the examination in a definite relationship to the image. It is not important whether this is carried out in a database or directly in additional storage locations for the image, e.g., according to the DICOM standard in which the data are stored in fixed connection to the image.

An automatic vessel detection device 7-1 is used for automatic vessel-dependent detection of vessel segments GS, which is also carried out depending upon the vessel type (artery or vein) and upon the image coordinates in an image, and correlates the vessel segment to a vessel portion at the same time.

By vessel segment GS is meant the smallest vascular unit that is geometrically resolved by a displayed or outputted vessel segment diameter, wherein the vessel, particularly a vessel portion, is formed by a plurality of vessel segments GS along the course of the vessel because a ring-shaped measurement zone is formed around the papilla by evaluation techniques, and the vessels present therein are studied as vessel portions.

Detected vessel segments GSd are sent to a measuring device for determining vessel diameter 7-2 which automatically measures a vessel diameter per detected vessel segment GSd along a vessel portion. It must be taken into account in some instances that a vessel segment diameter cannot be determined for every vessel segment.

The vessel segment diameter is determined at least at one measurement location in the vessel segment GSd, but preferably at a plurality of measurement locations through subsequent averaging, which has the advantage, aside from increased measuring certainty, that the diagonal attitude of the vessel extension can be corrected against the measurement line.

The determined (mean) vessel segment diameter can be displayed, outputted and, if necessary, stored while the individual measured values of measurement locations which are only stored temporarily are discarded and are no longer available for further processing when the vessel segment diameter is available after being calculated.

It is not important whether the automatic vessel detection device 7-1 and the measuring device for determining vessel diameter 7-2 are constructed as separate devices or form a common device or whether the detection of vessel segments GS, the detection of vessel type, the measurement of diameters, the determination of image coordinates, and the correlation of the vessel segments GS to a vessel portion are carried out in individual steps or combined in an optional manner or carried out in only one step, e.g., by means of a vessel tracker which is guided segment-by-segment along the measurement zone and also detects the starting point itself However, it is crucial that the vessel segments GS are fixedly stored with their correlations and mean vessel segment diameters and are accordingly available for subsequent evaluations.

Therefore, those vessel segments GSd for which a vessel segment diameter is available are sent as vessel segments GSi along with this vessel segment diameter to a vessel segment storage 7-3 where they are stored and archived with their correlation to the evaluated individual image EB, to the vessel portion, vessel type and image coordinates and to a reference image RB. Accordingly, preferably every vessel segment obtains its own data set containing the vessel segment diameter, the vessel segment coordinates in the evaluated image, the correlation with the vessel portion, the correlation with the vessel type (artery or vein), and a relatedness to the evaluated image. The relation to the examination data and patient data and to the examined eye can also be produced by means of the relatedness to the evaluated image.

An evaluating unit 7-4 for determining parameters in the vessel analysis calculates and temporarily stores parameters KG from the data sets for the vessel segments GSi. Parameters KG of this kind include the central arteriolar equivalent CAE and the central venular equivalent CVE which, by means of a known model formula, combine the determined diameters of the arteriolar and venular vessels located within a ring-shaped measurement zone surrounding the papilla and the ratio CAE(PSH)/CVE(PSH) from the two parameters, the arteriole-to-venule ratio (A/V(PSH) ratio).

The documenting of the individual image results obtained in the vessel analysis is carried out by a vessel analysis documenting unit 7-5. Vessel analysis logs and clinical state images are produced in which the vessel segment diameters or the spatially resolved parameters are displayed, e.g., in color-coded manner, for facilitated assessment.

An image selection device 8 is used for selecting first images to be studied or a reference image RB together with an associated comparison image VB or together with a series of comparison images. Comparison images VB are images which are recorded at a time offset with respect to a reference image RB and by means of which changes in the patient's eye can be determined.

If reference measurements are to be carried out, the image selection device 8 initially offers for selection all relevant images of the patient's eye that have already been evaluated. Then, all other images of this patient's eye that have or have not been evaluated are offered for selection as a comparison image. An entire series of comparison images can also be put together and can be worked up in sequence with reference to a reference image.

Coordinate conversion means 9 associated with the means (10) for retrieving identical vessel segments define displacement vectors by which the actual position of identical vessel segments in a comparison image VB or features of a comparison image VB can be converted into the reference image RB.

Suitable means for coordinate conversion are known from the prior art and calculate the displacement vectors of identical image points between two images. In the simplest case, image correlation methods which only determine the displacement in two vertical coordinates can be used, so that the same displacement coordinates would apply for all image points. However, methods which can calculate a displacement vector by segment or by image point are more precise.

A difference generator 7-6 is provided for determining measurement-specific and parameter-specific differences between a reference image RB and at least one comparison image VB and for providing progress images or alteration images or charts for the parameters, for which purpose differences between the measured vessel segment diameters and the parameters are generated.

While the foregoing description and drawings represent the present invention, it will be obvious to those skilled in the art that various changes may be made therein without departing from the true spirit and scope of the present invention.

What is claimed is:

1. A method for the analysis of retinal vessels based on digital images comprising the steps of:
   arranging a ring-shaped measurement zone containing vessel portions which proceed from a central vessel and are to be measured and which differ in type between arteries and veins, said zone being arranged around the papilla at a distance therefrom;
   determining a vessel diameter for each of these vessel portions;

calculating parameters from the determined vessel diameters of the vessel portions;
selecting a series of adjoining vessel segments along the vessel portions;
determining a vessel segment diameter and the associated image coordinates for every vessel segment;
correlating the vessel segments to a vessel type distinguished by artery or vein and to a vessel portion;
storing and archiving a data set comprising at least the coordinates of the vessel segment, the vessel segment diameter, the associated vessel type, the associated vessel portion, and a relatedness to the evaluated image for every vessel segment;
determining, by patient-oriented comparison measurements in comparison images recorded with a time offset with respect to a reference image, the diameters of vessel segments in the comparison image which are identical to the vessel segments in the reference image, wherein the correlation of the vessel type and vessel portion to every vessel segment is adopted intact in the data set of the comparison image from the data set of the reference image, and wherein the data sets relating to the vessel segments in the comparison images are supplemented at least by the relatedness to the reference image; and
using only identical vessel segments for which a vessel segment diameter can be determined in all of the comparison images and in the reference image for determining the data set in comparison measurements of the comparison images, and wherein absolute and relative differences between the reference image and the comparison image are generated for the vessel diameters and parameters.

2. The method according to claim 1;
wherein, for the purpose of determining the vessel segments in the comparison image that are identical to the vessel segments in the reference image, the coordinates for vessel segments in the comparison image are calculated from the coordinates of the vessel segments in the reference image by means of previously determined displacement vectors so that the measurement of the diameters of vessel segments in the comparison image that are identical to the vessel segments in the reference image can be carried out automatically, and wherein the data sets of the vessel segments of the comparison image are expanded at least by the displacement vector of the vessel segment.

3. The method according to claim 1;
wherein a mean diameter used for determining parameters is formed as an arithmetic average for every vessel portion from the progression of vessel segment diameters.

4. The method according to claim 3;
wherein, as first and second parameters, a central arteriolar equivalent and a central venular equivalent are determined from the mean diameters of the arteriolar vessel portions and the venular vessel portions and, as a third parameter, an arteriole-to-venule ratio is derived therefrom.

5. The method according to claim 4;
wherein the central arteriolar equivalent and the central venular equivalent are formed as nth roots from the sum of all nth powers of the mean vessel portion diameters, wherein a value for n between 2.5 and 3.0 is used for the central arteriolar equivalent, and a value for n between 2.0 and 2.5 is used for the central venular equivalent.

6. The method according to claim 1;
wherein a maximum diameter and a minimum diameter and the scatter of the mean vessel segment diameters are determined for every vessel portion as a fourth parameter vector.

7. The method according to claim 1;
wherein the reciprocal of the fourth power of the mean vessel segment radius is formed as a fifth parameter for describing the vascular resistance of a vessel segment.

8. The method according to claim 1;
wherein the quotient of the vessel length and vessel radius is formed as a sixth parameter for describing the local pressure drop.

9. The method according to claim 1;
wherein an inside value and an outside value, respectively; for a central arteriolar equivalent, a central venular equivalent and an arteriole-to-venule ratio are formed from the mean vessel diameters of the vessel portions which lie closest to the inside boundary of the ring-shaped measurement zone and from the mean vessel diameters of the vessel portions lying closest to the outside boundary of the ring-shaped measurement zone.

10. The method according to claim 4;
wherein a seventh parameter, an eighth parameter and a ninth parameter are formed:
as root from the sum of all squares of the mean diameters of a vessel portion,
as third root from the sum of all third powers of the mean diameters of a vessel portion,
as fourth root from the sum of all fourth powers of the mean diameters of a vessel portion, and
wherein the central equivalents for arteries and veins are determined from the seventh, eighth and ninth parameters, and the arteriole-to-venule ratio is formed from these central equivalents.

11. The method according to claim 10;
wherein parameters are determined for every vessel portion for a focal narrowing, their absolute value being arrived at as follows, where threshold values are given as percentages:
first parameter focal narrowing $N1$=percentage threshold value for $N1 \times$ mean diameter of the vessel portion/100%,
second parameter focal narrowing $N2$=percentage threshold value for $N2 \times$ seventh parameter/100%,
third parameter focal narrowing $N3$=percentage threshold value for $N3 \times$ eighth parameter/100%, and
fourth parameter focal narrowing $N4$=percentage threshold value for $N4 \times$ ninth parameter/100%.

12. The method according to claim 1;
wherein differences between spatially resolved parameters of the comparison image and of the reference image are calculated, and in that different images are generated from the reference image, in which different images the diameter differences or spatially resolved parameters or spatially resolved parameter differences determined, respectively, from the comparison measurements are entered in correct coordinates and with color coding.

13. The method according to claim 1;
wherein progress graphics are produced in which the vessel diameters and/or the parameters or differences thereof between comparison images and the reference image are graphically represented as a function of the time of the image recording.

14. The method according to claim 1;
wherein the determined parameters and parameter differences are logged in a summarized manner for data output.

15. The method according to claim 3;
wherein the positions of the vessel segments are marked in the evaluated image in such a way that the vessel segment diameter is reproduced in a coded manner or the vessel portion is characterized.

* * * * *